(12) United States Patent
Gunji et al.

(10) Patent No.: US 6,303,381 B1
(45) Date of Patent: Oct. 16, 2001

(54) INSERTION SEQUENCE

(75) Inventors: Yoshiya Gunji; Hisashi Yasueda; Yoshio Kawahara; Shinichi Sugimoto, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/455,921

(22) Filed: Dec. 7, 1999

(30) Foreign Application Priority Data

Dec. 8, 1998 (JP) .................................................. 10-348374

(51) Int. Cl.⁷ .......................... C12N 15/00; C12N 15/11; C12Q 1/68; C07H 21/04
(52) U.S. Cl. .............................. 435/473; 435/471; 435/6; 536/23.1; 536/23.2; 536/23.7; 536/24.1; 536/24.3; 536/24.32
(58) Field of Search .................................. 536/23.1, 23.2, 536/23.7, 24.1, 24.3, 24.32; 435/6, 471, 473

(56) References Cited

PUBLICATIONS

T.M. Barta, et al., Antonie Van Leeuwenhoek Int. J. Gen. Mol. MicroBiol., vol. 64, No. 2, pp. 109–120, "Genetics of Methane and Methanol Oxidation in Gram–Negative Methylotroph Bacteria," 1993.

A.C. Satinthorpe, Gene, vol. 91, pp. 27–34, "The Methane Monooxygenase Gene Cluster of Methylococcus Capsulatus (Bath)," 1990.

*Primary Examiner*—Andrew Wang
*Assistant Examiner*—Mark L. Shibuya
(74) *Attorney, Agent, or Firm*—Oblon, Spivak, McClelland, Maier & Neustadt, P.C.

(57) ABSTRACT

A novel insertion sequence, which has been found in the sMMO gene coding for methane monooxygenase of methane-assimilating bacterium *Methylococcus capsulatus* NCIMB 11132 strain, and has inverted repeat sequences consisting of a sequence of the nucleotide numbers 5–19 of SEQ ID NO: 1 at the both ends, can be utilized as effective means for genetic analysis including creation of insertion mutant strains, gene mapping, promoter searching, insertion of genetic information into chromosomal DNA, disruption of specific gene and the like, or utilized for improving methane-assimilating bacteria by chromosomal genetic engineering techniques.

17 Claims, 1 Drawing Sheet

SEQUENCE LISTING

<160> NUMBER OF SEQ ID NOS: 4

<210> SEQ ID NO 1
<211> LENGTH: 1343
<212> TYPE: DNA
<213> ORGANISM: Methylococcus capsulatus
<220> FEATURE:
<221> NAME/KEY: CDS
<222> LOCATION: (90)..(1115)

<400> SEQUENCE: 1

```
ttaacaggcc gttgaaaaac tcccccgcag ccgcccgtgc tgccggtacc atgtgagcgg      60
cggcgacgac gagacagcag acaccgaag atg aga ggc aca cag aac ttc caa      113
                                 Met Arg Gly Thr Gln Asn Phe Gln
                                  1               5 ggg gcg atg ttc agc tac atc agc ctt gaa gag cgg gta ccg gcc aga      161
Gly Ala Met Phe Ser Tyr Ile Ser Leu Glu Glu Arg Val Pro Ala Arg
         10                  15                  20 cac ccg ctg cgc aag ctg cgc gcg ctg gtc gat gcc ttg ctg gcc agc      209
His Pro Leu Arg Lys Leu Arg Ala Leu Val Asp Ala Leu Leu Ala Ser
 25                  30                  35                  40
```

-continued

| | |
|---|---|
| atg agc gcg gaa ttc gag gcg gtc tat gcc cgc cgt ggc cgc cct tcg<br>Met Ser Ala Glu Phe Glu Ala Val Tyr Ala Arg Arg Gly Arg Pro Ser<br>                            45                      50                  55 | 257 |
| gtg ccg ccc gaa atg ctg ctc aag gcg ttg ctg ctg caa atc ctg ttt<br>Val Pro Pro Glu Met Leu Leu Lys Ala Leu Leu Leu Gln Ile Leu Phe<br>                  60                    65                      70 | 305 |
| tcc atc cgc agc gag cgg ctg ctg gtg gag gcc atc gac tac aac ctg<br>Ser Ile Arg Ser Glu Arg Leu Leu Val Glu Ala Ile Asp Tyr Asn Leu<br>           75                      80                    85 | 353 |
| ctg tac cgc tgg ttc gtg ggc ctg aac tgg aag aca agg tgt ggg acc<br>Leu Tyr Arg Trp Phe Val Gly Leu Asn Trp Lys Thr Arg Cys Gly Thr<br>        90                  95                    100 | 401 |
| act cca cct tca gcg cca acc gcc agc ggc tgt tca acg aaa gac ctc<br>Thr Pro Pro Ser Ala Pro Thr Ala Ser Gly Cys Ser Thr Lys Asp Leu<br>105                      110                    115                  120 | 449 |
| gcc cgc gtg ttc ttt gag cgg gtc aaa tac acc gcg gac tgg gcg aag<br>Ala Arg Val Phe Phe Glu Arg Val Lys Tyr Thr Ala Asp Trp Ala Lys<br>                  125                  130                  135 | 497 |
| ttg atc ggt gac gag cac ttc agc gtc gac ggc aca ctc atc gag gcc<br>Leu Ile Gly Asp Glu His Phe Ser Val Asp Gly Thr Leu Ile Glu Ala<br>            140                    145                  150 | 545 |
| tgg gcc tcg caa aag agc ttc aag cgc aag gac gca agc ggc agt gac<br>Trp Ala Ser Gln Lys Ser Phe Lys Arg Lys Asp Ala Ser Gly Ser Asp<br>                155                  160                  165 | 593 |
| gac ggc gca ccg ccc cag ggt cgc aac ccc gag gtg gat ttc aag ggc<br>Asp Gly Ala Pro Pro Gln Gly Arg Asn Pro Glu Val Asp Phe Lys Gly<br>170                      175                    180 | 641 |
| gag acc cgt cgc aac gac acc cac gcc agc acg aca gat gcc gat gcg<br>Glu Thr Arg Arg Asn Asp Thr His Ala Ser Thr Thr Asp Ala Asp Ala<br>185                      190                    195                  200 | 689 |
| cgg ctg ttc aag aaa gct gca ggc gac aag tcc cgc ctg tgc cac atg<br>Arg Leu Phe Lys Lys Ala Ala Gly Asp Lys Ser Arg Leu Cys His Met<br>                205                  210                  215 | 737 |
| ggt cac atc ctc atg gac aac cga cac ggg ctg gtg gtg gac gtc gaa<br>Gly His Ile Leu Met Asp Asn Arg His Gly Leu Val Val Asp Val Glu<br>            220                    225                  230 | 785 |
| atc acc cat gcc agc ggc acg gcc gag cgg cag gcc gca ctc aag atg<br>Ile Thr His Ala Ser Gly Thr Ala Glu Arg Gln Ala Ala Leu Lys Met<br>                235                  240                  245 | 833 |
| ctc cag cgc caa aag cgc aaa gcc ggc cga ctc acc gtg ggg gcg gac<br>Leu Gln Arg Gln Lys Arg Lys Ala Gly Arg Leu Thr Val Gly Ala Asp<br>250                      255                    260 | 881 |
| aag ggc tat gac tgc cgt gcc ttc gtg cag ggc tgc cgc aag ctg ggg<br>Lys Gly Tyr Asp Cys Arg Ala Phe Val Gln Gly Cys Arg Lys Leu Gly<br>265                      270                    275                  280 | 929 |
| atc acc ccg cac gtg gcg gcc aaa gcc aag cac tcg gcc att gac gga<br>Ile Thr Pro His Val Ala Ala Lys Ala Lys His Ser Ala Ile Asp Gly<br>                285                  290                  295 | 977 |
| cgc acc cag cgg cac gaa ggc tac aag gtg agc ctg agg tgc gca aac<br>Arg Thr Gln Arg His Glu Gly Tyr Lys Val Ser Leu Arg Cys Ala Asn<br>300                      305                    310 | 1025 |
| gca tcg agg agc att tcg gct gga tca aga ccg tgg gcg gtc tgg cca<br>Ala Ser Arg Ser Ile Ser Ala Gly Ser Arg Pro Trp Ala Val Trp Pro<br>315                      320                    325 | 1073 |
| aga cca agc tca tcg ggc atg cca agc tgg cgg ggc agg cgc<br>Arg Pro Ser Ser Ser Gly Met Pro Ser Trp Arg Gly Arg Arg<br>330                      335                    340 | 1115 |
| tgatgtgctt tgccgcgtac aacctcgtgc gcatgggctc cctcggtggc tggtgggatg | 1175 |

```
cgcatcatgc gtgattgcgg gggtcagtgc gcccaaaatg ggcgagcagc tcccaatggg    1235
ggagcccaag ccgctgccgg agccgagaaa acggcttgc gccggcctcg gacccacgca    1295
aacgggtaca tggccgcttc gatggacact ttttcaacgg cctgttaa                1343
```

<210> SEQ ID NO 2
<211> LENGTH: 342
<212> TYPE: PRT
<213> ORGANISM: Methylococcus capsulatus

<400> SEQUENCE: 2

```
Met Arg Gly Thr Gln Asn Phe Gln Gly Ala Met Phe Ser Tyr Ile Ser
  1               5                  10                  15

Leu Glu Glu Arg Val Pro Ala Arg His Pro Leu Arg Lys Leu Arg Ala
             20                  25                  30

Leu Val Asp Ala Leu Leu Ala Ser Met Ser Ala Glu Phe Glu Ala Val
         35                  40                  45

Tyr Ala Arg Arg Gly Arg Pro Ser Val Pro Pro Glu Met Leu Leu Lys
     50                  55                  60

Ala Leu Leu Leu Gln Ile Leu Phe Ser Ile Arg Ser Glu Arg Leu Leu
 65                  70                  75                  80

Val Glu Ala Ile Asp Tyr Asn Leu Leu Tyr Arg Trp Phe Val Gly Leu
                 85                  90                  95

Asn Trp Lys Thr Arg Cys Gly Thr Thr Pro Pro Ser Ala Pro Thr Ala
            100                 105                 110

Ser Gly Cys Ser Thr Lys Asp Leu Ala Arg Val Phe Phe Glu Arg Val
        115                 120                 125

Lys Tyr Thr Ala Asp Trp Ala Lys Leu Ile Gly Asp Glu His Phe Ser
    130                 135                 140

Val Asp Gly Thr Leu Ile Glu Ala Trp Ala Ser Gln Lys Ser Phe Lys
145                 150                 155                 160

Arg Lys Asp Ala Ser Gly Ser Asp Asp Gly Ala Pro Pro Gln Gly Arg
                165                 170                 175

Asn Pro Glu Val Asp Phe Lys Gly Glu Thr Arg Arg Asn Asp Thr His
            180                 185                 190

Ala Ser Thr Thr Asp Ala Asp Ala Arg Leu Phe Lys Lys Ala Ala Gly
        195                 200                 205

Asp Lys Ser Arg Leu Cys His Met Gly His Ile Leu Met Asp Asn Arg
    210                 215                 220

His Gly Leu Val Val Asp Val Glu Ile Thr His Ala Ser Gly Thr Ala
225                 230                 235                 240

Glu Arg Gln Ala Ala Leu Lys Met Leu Gln Arg Gln Lys Arg Lys Ala
                245                 250                 255

Gly Arg Leu Thr Val Gly Ala Asp Lys Gly Tyr Asp Cys Arg Ala Phe
            260                 265                 270

Val Gln Gly Cys Arg Lys Leu Gly Ile Thr Pro His Val Ala Ala Lys
        275                 280                 285

Ala Lys His Ser Ala Ile Asp Gly Arg Thr Gln Arg His Glu Gly Tyr
    290                 295                 300

Lys Val Ser Leu Arg Cys Ala Asn Ala Ser Arg Ser Ile Ser Ala Gly
305                 310                 315                 320

Ser Arg Pro Trp Ala Val Trp Pro Arg Pro Ser Ser Gly Met Pro
                325                 330                 335

Ser Trp Arg Gly Arg Arg
            340
```

```
<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
ggtaagttta tgcagcgagt tcacactatc acggcggt                              38

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
tcgcatgaag gggccaagtc cggcggggcc                                       30
```

INSERTION SEQUENCE

TECHNICAL FIELD

The present invention relates to a novel insertion sequence derived from a methane-assimilating bacterium. Because the insertion sequence may be transposed or inserted into various sites on chromosomes, it can be utilized as effective means for genetic analysis or means for incorporating a desired gene into a bacterial chromosome.

BACKGROUND ART

As for both of prokaryotes and eukaryotes, DNA sequences transposable from one site to another site within a genome or between different genomes have been known, and generally called transposable elements. Most of such transposable elements encode, within their own sequences, a site-specific recombination enzyme (transposase) required for the translocation from one site to another site. Among such transposable elements, those having the smallest and simplest structure are called insertion sequence (IS).

Insertion sequences among microbial transposable sequences exhibit several characteristics. They have a size of about 1 to 2 kb, and have inverted repeat sequences of about 8–20 bp at the both ends. When an insertion sequence is inserted into a microbial chromosome, duplication of a target sequence occurs on the end side of the insertion sequence (Mobile Genetic Elements, Academic Press, New York, p.159–221 (1983)). Among microbial insertion sequences, well studied are those derived from *Escherichia coli* [Mol. Gen. Genet., Vol. 122, 267–277 (1973)], those derived from Shigella [*J. Bacteriol.*, 172, 4090–4099 (1993)], those derived from acetic acid bacteria [*Mol. Microbiol.*, 9, 211–218 (1993)], those derived from mycoplasma [*Mol. Microbiol.*, 7, 577–584 (1993)] and the like.

On the other hand, as for methane-assimilating bacteria, there have been known inventions of a method for continuous production of oxidation products utilizing such bacterial cells (Japanese Patent Laid-open No. 5-3279, Japanese Patent Laid-open No. 54-3583), environmental cleanup through degradation of environmental pollutants utilizing methane-assimilating bacteria (Japanese Patent Laid-open No. 6-245761, Japanese Patent Laid-open No. 8-24905), fermentation method for converting methane into materials for protein production (Japanese Patent Laid-open No. 50-40788) and the like. Thus, they are industrially important microorganisms. However, any insertion sequence derived from methane-assimilating bacteria has not been reported so far.

SUMMARY OF THE INVENTION

During the cloning of a gene coding for methane monooxygenase (it may be abbreviated as "sMMO gene" hereinafter) for functional analysis of the methane monooxygenase (it may be abbreviated as "sMMO" hereinafter), which is an enzyme derived from a methane-assimilating bacteria, *Methylococcus capsulatus,* the inventors of the present invention found that an insertion sequence was contained in that gene. The present invention has been accomplished based on this finding.

That is, the present invention provides an insertion sequence which has the nucleotide sequence shown in SEQ ID NO: 1 derived from chromosomal DNA of a Methylococcus bacterium. The present invention also provides an insertion sequence which has the inverted repeat sequences at the both ends, wherein each of the inverted repeat sequences consists of a sequence of the nucleotide numbers 5–19 of SEQ ID NO: 1.

DETAILED DESCRIPTION OF THE INVENTION

Figure 1:
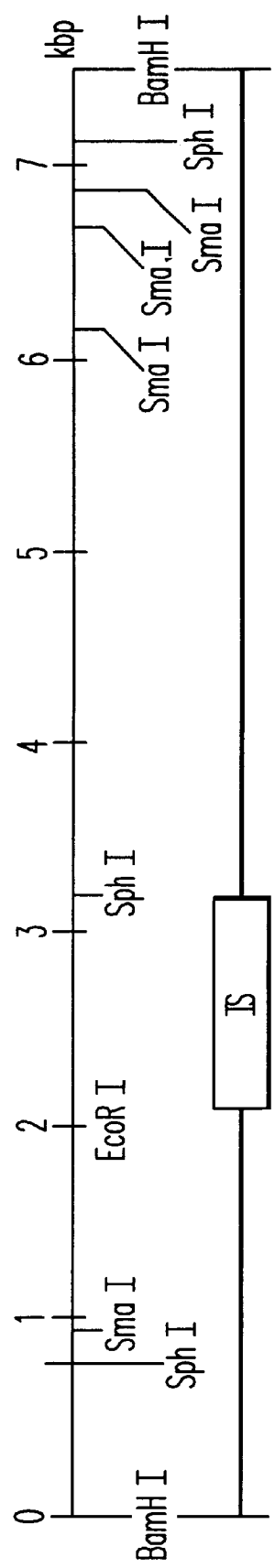
FIG. 1 is a restriction map of a DNA fragment containing a part of the sMMO gene having an insertion sequence of the present invention. The box represents an open reading frame in the insertion sequence.

Hereafter, the present invention will be explained in detail.

The insertion sequence of the present invention was found in the sMMO gene of a methane-assimilating bacterium, *Methylococcus capsulatus* NCIMB 11132 strain, and can be obtained by isolating it from a chromosomal DNA of the strain. An exemplary method for obtaining this insertion sequence will be explained below.

Anyone can obtain the *Methylococcus capsulatus* NCIMB 11132 strain from NCIMB (National Collection of Industrial and Marine Bacteria Ltd., 23 St. Machar Drive, Aberdeen AB21RY, Scotland, UK). While medium used for culturing the NCIMB 11132 strain is not particularly limited so long as the bacterium can sufficiently proliferate in it, the medium of Whittenberry et al. (*J. Gen. Microbiol.*, 61, pp.205–208, 1970) can be mentioned as a suitable medium, for example. A space of culture vessel containing a medium is replaced with a mixed gas of methane and oxygen-containing gas (air etc.), and the NCIMB 11132 strain is inoculated to the medium contacting with the gas. The *Methylococcus capsulatus* used for the present invention is an aerobic bacterium, and may be cultured at 20–50° C. under an aerobic condition as a batch culture or continuous culture.

A DNA fragment containing the sMMO gene can be obtained by preparing a DNA fragment containing a part of the sMMO gene through PCR (polymerase chain reaction) utilizing oligonucleotides prepared based on the nucleotide sequence of a known sequence of the gene as primers, and isolating the target fragment from a DNA library obtained from chromosome of *Methylococcus capsulatus* strain through hybridization utilizing the above-prepared DNA fragment as a probe in a manner as described below.

The chromosomal DNA can be extracted from culture solution of the *Methylococcus capsulatus* NCIMB 11132 strain by a conventional method which has been known per se (see, for example, *Biochem. Biophys. Acta.*, 72, 619] (1963)).

The DNA library can be prepared by digesting chromosomal DNA with a suitable restriction enzyme such as BamHI, ligating the resulting DNA fragments of various sizes to a plasmid vector such as pUC18 (produced by Takara Shuzo), and transforming a suitable host such as *Escherichia coli* JM109 by using the ligation solution.

The probe used for selecting clones having the DNA fragment containing the sMMO gene by the hybridization can be obtained by PCR which utilizes oligonucleotides having the nucleotide sequences suitably established from the known nucleotide sequence of the sMMO gene, for example, the nucleotide sequences of SEQ ID NOS: 3 and 4 as primers and chromosomal DNA of *Methylococcus capsulatus* as a template.

By using a probe obtained as described above, colony hybridization is performed for the chromosomal DNA library of the *Methylococcus capsulatus* NCIMB 11132 strain. A DNA fragment containing the insertion sequence of the present invention can be obtained by extracting plasmid DNA from clones that hybridize with the probe, i.e., the partial DNA fragment of the sMMO gene in the hybridization, and digesting the plasmid with a restriction enzyme BamHI to obtain the insertion sequence.

A restriction map of 7.5 kbp BamHI fragment obtained in the example mentioned below is represented in FIG. 1. A plasmid vector pHSG398(produced by Takara Shuzo CO., LTD.) containing a fragment of about 5.0 kbp excised with SmaI from the 7.5 kbp fragment (also referred to as "SmaI fragment" hereinafter) was designated as pHSMO50. An *E. coli* strain JM109 harboring this plasmid pHSMO50 (AJ13497) was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 16, 1998, as an accession number of FERM P-17024, and transferred from the original deposit to international deposit based on Budapest Treaty on Nov. 24, 1999, and has been deposited as an accession number of FERM BP-6947.

A DNA fragment containing the insertion sequence of the present invention can be obtained by preparing a plasmid from this deposited strain and excising a SmaI fragment from this plasmid.

The nucleotide sequence of the insertion sequence of the present invention obtained as described above is shown in SEQ ID NO: 1. In this nucleotide sequence, it is expected that AATT sequences of the nucleotide numbers 1–4 and the nucleotide numbers 1340–1343 are the target sequences. The sequences of the nucleotide numbers 5–19 and 1325–1339 each internally adjacent to the target sequences are the inverted repeat sequences.

In addition to the aforementioned method, the insertion sequence of the present invention can also be directly amplified from chromosome DNA of the *Methylococcus capsulatus* NCIMB 11132 strain by PCR utilizing oligonucleotides synthesized based on the nucleotide sequence of SEQ ID NO: 1 as primers.

The insertion sequence of the present invention can be used for the same applications as those of known insertion sequences. For example, it can be utilized for analysis of mechanisms of gene disruption, gene amplification and gene expression in methane-assimilating bacteria.

Further, the insertion sequence of the present invention and the inverted repeat sequence contained in the insertion sequence can be utilized for the construction of an artificial transposon. Transposons include those having a gene such as drug resistance gene between two insertion sequences, and those having a gene such as drug resistance gene inserted into the insertion sequence. Therefore, a transposon can be constructed by sandwiching a desired gene with the insertion sequences of the present invention. Alternatively, an insertion sequence or a transposon can be constructed by sandwiching a desired gene with the aforementioned inverted repeat sequences.

Transposition of an insertion sequence or transposon requires transposase, and an insertion sequence usually contains a transposase gene within it. An open reading frame of 1026 bp, which may code for a polypeptide consisting of 342 amino acid residues, was also found in the insertion sequence of the present invention (nucleotide numbers 90–1115 in SEQ ID NO: 1). While homology between the amino acid sequence of this polypeptide and known transposases has not been found, that sequence can be estimated to encode a transposase. An artificial transposon may be created by using this transposase.

Such a transposase gene may be present within an artificial transposon, and may be present outside the transposon. For example, the transposase gene may be carried by the same vector as the one carrying the artificial transposon, or the transposase gene may be carried by another vector other than the artificial transposon-carrying vector. Furthermore, the transposase gene may present on a chromosome of methane-assimilating bacteria.

The constructed artificial transposon is introduced into a suitable vector, and then introduced into a methane-assimilating bacterium which is a host. Examples of the methane-assimilating bacterium include, for example, bacterium belonging to the genus *Methylococcus*, *Methylomonas* or *Methylosinus* such as *Methylococcus capsulatus*, *Methylomonas albus*, and *Methylosinus trichosporium* and the like.

The plasmid for carrying the artificial transposon is not particularly limited, and a plasmid functioning in methane-assimilating bacteria may be used. Specifically, there can be mentioned R68.45, RP4, pVK100, derivatives of these plasmids containing drug resistance genes, and the like. As the method for introducing a plasmid into methane-assimilating bacteria, the method of Warner et al. (*FEMS Microbiol. Lett.*, 7, 181–185 (1980)) may be used.

By using an artificial transposon carrying a suitable drug resistance gene, and suitably selecting a drug concentration for selection of a host harboring the transposon, a gene amplified cells in which multiple copies of the artificial transposon are transposed on chromosomes can efficiently be obtained (see Japanese Patent Laid-open No. 9-70291).

The insertion sequence of the present invention can be transposed and inserted into various sites on chromosomes. By means of this ability, the insertion sequence of the present invention can be used as effective means for genetic analysis. Examples of the applications include, for example, creation of insertion mutant strains, gene mapping, promoter searching, insertion of genetic information, disruption of specific gene and the like. Moreover, methane-assimilating bacteria may be improved with the insertion sequence by using chromosomal genetic engineering techniques.

BEST MODE FOR CARRYING OUT THE INVENTION

The present invention will be further specifically explained with reference to the following examples.

<1>Preparation of Chromosomal DNA Library of Methane-assimilating Bacterium *Methylococcus capsulatus*

A space of culture vessel containing the medium of Whittenberry et al. [*J. Gen. Microbiol.*, 61, 205–208, 1970] was replaced with a mixed gas of methane and air. A methane-assimilating bacterium *Methylococcus capsulatus* NCIMB 11132 strain was inoculated to the medium in contact with the gas, and cultured under an aerobic condition as a batch culture with gas substitution.

Chromosomal DNA was extracted from the cells of *Methylococcus capsulatus* NCIMB 11132 cultured as described above according to the method described in *Biochem. Biophys. Acta.*, 72, 619 (1963). This chromosomal DNA was completely digested with a restriction enzyme BamHI. The obtained DNA fragments of various sizes were inserted into BamHI site of the plasmid vector pUC18 (produced by Takara Shuzo CO., LTD.). *Escherichia coli* JM109 strain was transformed with the obtained recombinant plasmids to produce a chromosomal DNA library.

<2>Cloning of sMMO Gene by Colony Hybridization

Clones containing the sMMO gene fragment were selected from the aforementioned chromosomal DNA library by colony hybridization. A probe for the hybridization was prepared by amplifying the sMMO gene fragment by PCR. The nucleotide sequence of the sMMO gene of *Methylococcus capsulatus* had been already reported [*Gene*, 91, 27–34 (1990)], and oligonucleotides having the nucleotide sequences of SEQ ID NO: 3 and SEQ ID NO: 4 were synthesized based on that sequence.

PCR was performed by using the chromosomal DNA of *Methylococcus capsulatus* prepared as described above as a template, and the aforementioned oligonucleotides as primers. The PCR was performed with a reaction cycle consisting of a denaturation step (94° C., 10 seconds), an annealing step (55° C., 30 seconds), and an extension step (72° C., 1 minute and 30 seconds), which was repeated for 30 cycles.

Colony hybridization was performed for the aforementioned chromosomal DNA library by using the partial fragment of the sMMO gene amplified as described above as a probe. Labeling of the probe and the hybridization reaction were performed by using DIG-High Prime DNA Labeling & Detection Starter Kit I (purchased from Boehringer Mannheim Co.) according to the attached protocol.

Recombinant plasmid DNA was extracted from the clones positive for the hybridization, and the plasmid DNA was digested with a restriction enzyme BamHI to confirm the inserted fragment. As a result, an inserted DNA fragment having a size of about 7.5 kb was confirmed in addition to the DNA fragment of the plasmid pUC18 having a length of about 2.3 kb. This recombinant plasmid was designated as pSMO75. A restriction map of this inserted fragment is represented in FIG. 1. Further, a fragment of about 5.0 kbp excised with SmaI (also referred to as "SmaI fragment" hereinafter) from the above fragment of about 7.5 kb excised with BamHI was subcloned in a plasmid vector pHSG398 (produced by Takara Shuzo CO., LTD.). This plasmid was designated as pHSMO50. An *E. coli* JM109 strain harboring this plasmid pHSMO50 was designated as AJ13497, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 16, 1998, as an accession number of FERM P-17024, and transferred from the original deposit to international deposit based on Budapest Treaty on Nov. 24, 1999, and has been deposited as an accession number of FERM BP-6947.

The nucleotide sequence of the aforementioned SmaI fragment was determined by the dideoxy chain termination method [Proc. Natl. Acad. Sci., USA, 74, 5463 (1997)].

By cloning the sMMO gene of the *Methylococcus capsulatus* NCIMB 11132 strain and determining its nucleotide sequence as described above, it was confirmed that an insertion sequence was present in the sMMO gene. The nucleotide sequence of this insertion sequence is shown in SEQ ID NO: 1.

Nucleotide sequence analysis of the above sequence revealed that that the sequence of TTAA at the 1st to 4th positions was also recognized as a sequence of the 1340th to 1343rd positions, and they were the target sequences, and also revealed that complementary strands of a sequence from C at the 5th position to A at the 19th position and a sequence from T at the 1325th position to G at the 1339th position each internally adjacent to the target sequences were identical, and they were the inverted repeat sequences. Based on these findings, these parts were confirmed to be the insertion sequences.

Further detailed analysis of the insertion sequence determined as described above revealed presence of an open reading frame of 1026 bp from A at the 90th position to A at the 1115th position. An amino acid sequence consisting of 342 residues that can be translated from the sequence (a sequence starting with Met encoded by ATG) is shown in SEQ ID NO: 1 and SEQ ID NO: 2. The molecular weight of the protein anticipated from this amino acid sequence was about 38,000. A database was searched by computer for an amino acid sequence exhibiting homology to the above amino acid sequence, but any known amino acid sequences having high homology were not retrieved.

What is claimed is:

1. An isolated polynucleotide consisting of SEQ ID NO:1.

2. The isolated polynucleotide of claim 1, which is derived from chromosomal DNA of a *Methylococcus* bacterium.

3. A plasmid comprising the isolated polynucleotide of claim 1.

4. An artificial transposon comprising a target gene interposed between nucleotides 5–19 of SEQ ID NO:1 and nucleotides 1325–1339 of SEQ ID NO:1.

5. The artificial transposon of claim 4, further comprising nucleotides 90–1115 of SEQ ID NO:1.

6. The artificial transposon of claim 4, further comprising nucleotides 1–4 of SEQ ID NO:1 and nucleotides 1340–1343 of SEQ ID NO:1.

7. A plasmid comprising the artificial transposon of claim 6.

8. A method of inserting a target gene into a chromosome comprising contacting a cell containing the chromosome with the artificial transposon of claim 7.

9. A method of inserting a target gene into a chromosome comprising contacting a cell containing the chromosome with the artificial transposon of claim 6.

10. The method of claim 9, wherein said target gene is a drug resistance gene.

11. The artificial transposon of claim 4, wherein said target gene is a drug resistance gene.

12. A plasmid comprising the artificial transposon of claim 11.

13. A plasmid comprising the artificial transposon of claim 4.

14. A method of inserting a target gene into a chromosome comprising contacting a cell containing the chromosome with the plasmid of claim 13 a vector comprising nucleotides 1340–1343.

15. A method of inserting a target gene into a chromosome comprising contacting a cell containing the chromosome with the artificial transposon of claim 4 and a vector comprising nucleotides 1340–1343.

16. The method of claim 15, wherein said target gene is a drug resistance gene.

17. A method of inserting a target gene into a chromosome comprising contacting a cell containing the chromosome with the plasmid of claim 3.

* * * * *